United States Patent [19]

Long et al.

[11] Patent Number: 5,275,596
[45] Date of Patent: Jan. 4, 1994

[54] LASER ENERGY DELIVERY TIP ELEMENT WITH THROUGHFLOW OF VAPORIZED MATERIALS

[75] Inventors: Gary Long, Cincinnati, Ohio; Richard L. Studer, Villa Hills, Ky.

[73] Assignee: Laser Centers of America, Cincinnati, Ohio

[21] Appl. No.: 812,449

[22] Filed: Dec. 23, 1991

[51] Int. Cl.[5] .............................................. A61B 17/36
[52] U.S. Cl. ...................................... 606/28; 606/27; 606/15; 606/16
[58] Field of Search ............ 606/2; 3, 7, 10, 16, 27, 28, 37, 38, 39, 40, 41, 45, 49; 128/397,358

[56] References Cited

U.S. PATENT DOCUMENTS

| | | | |
|---|---|---|---|
| 3,898,991 | 8/1975 | Ikuno et al. | 606/37 |
| 4,233,493 | 11/1980 | Nath | 128/398 X |
| 4,334,539 | 6/1982 | Childs et al. | 606/37 |
| 4,654,024 | 3/1987 | Crittenden et al. | 606/28 |
| 4,736,743 | 4/1988 | Diakuzono | 606/28 X |
| 4,760,845 | 8/1988 | Kovalcheck | 606/28 |
| 4,832,979 | 5/1989 | Hoshino et al. | 606/28 |
| 5,071,222 | 12/1991 | Laakmann et al. | 606/28 X |

*Primary Examiner*—Peter A. Aschenbrenner
*Attorney, Agent, or Firm*—Lowe, Price, LeBlanc & Becker

[57] ABSTRACT

A laser energy delivery tip element for applying laser energy received through an optical fiber has a foraminous element disposed to receive laser light energy emitted from the optical fiber to be heated thereby. The heated portion of the foraminous element is disposed to be contacted to a tissue so as to heat and vaporize a portion of the tissue to form an incision. Suction is applied to the laser energy tip element to immediately draw away from the incision site any gaseous and/or vaporized substances generated during its use to apply heat, the sucked-away substances passing through openings in the foraminous element and around and outside the optical fiber, to thereby facilitate viewing of the incision-making activity. In another aspect of the invention, a separately controlled electrical voltage is applied through the foraminous element to generate a relatively high current over a small area of the patient's incised tissue to, for example, cauterize a cut blood vessel, the current passing through a relatively large surface area of the patient to an electrically conducting support element. A surgeon utilizing such a laser energy tip element with separate control over a cauterizing current can thus employ a single hand-held surgical tool to cut through tissues, cauterize any cut blood vessels, and simultaneously remove any gaseous and/or vaporized substances generated by either the laser-cutting or electro-cautery actions.

23 Claims, 4 Drawing Sheets

LASER ENERGY DELIVERY TIP ELEMENT WITH THROUGHFLOW OF VAPORIZED MATERIALS

FIELD OF THE INVENTION

This invention relates to a tip element for delivering laser energy for localized application, and more particularly to a tip element that facilitates immediate removal of gaseous and/or vaporized substances produced by the application of laser energy in surgical functions such as incision and cauterization of incised blood vessels.

BACKGROUND OF THE PRIOR ART

Many laser surgical systems are known in which a hand-held surgical device is applied by a surgeon to deliver laser energy to tissues at such a rate that the affected tissues disintegrate into gaseous and/or vaporized substances. Such a delivery of laser energy, for example to effect localized incisions, generally requires a relatively small tip element shaped and oriented to enable the surgeon to see clearly where the laser energy is being delivered. It is inevitable in surgery that blood vessels are occasionally incised, whether the surgeon is applying a scalpel or a laser surgical tool. To prevent undesirable bleeding from the cut blood vessel, the surgeon or an assistant typically cauterizes the incised blood vessel as quickly as possible. Such cauterization may require separate tools, but certain versatile laser energy delivering tip elements are also known which enable a user to selectively apply the same tool to effect either incisions or cauterization of incised vessels Regardless of how good the local ventilation is in an operating room, a surgeon performing precise incision/cauterization with a laser surgical tool must contend with the presence of unpleasant odors, smoke and the gaseous and/or vaporized byproducts of the heated tissues every time he or she applies laser energy. Surgeons and their operating room assistants would experience less stress and be able to function more efficiently if the gaseous and/or vaporized substances produced during surgery and cauterization were immediately removed from the site where they are produced.

A need, therefore, clearly exists for an improved laser energy delivery tip element which enables a user to remove gaseous and/or vaporized substances immediately upon their production during surgery and cauterization.

Furthermore, even though versatile laser energy delivery tip elements are known which are useful for both incision making and for cauterization, to simplify the surgeon's task in operating the hand-held laser surgical tool, it is also highly desirable to provide the surgeon with a separately operated cauterization system in which controlled amounts of heat can be selectively delivered by the incision-making tip element itself without the need for separate tools or additional hand-operated actuation elements.

The present invention, as described more fully hereinbelow and as illustrated in its essentials in the accompanying drawing figures, is intended to meet both of these needs, i.e., to immediately remove gaseous and/or vaporized substances from the surgical site and, with the same tip element, to enable the surgeon to selectively deliver controlled amounts of energy to effect cauterization by a foot-actuated control.

SUMMARY OF THE INVENTION

Accordingly, it is a principal object of this invention to provide a laser energy delivery tip element suitable for use in a hand-held surgical tool to deliver laser energy to perform surgical incisions while, simultaneously, facilitating the immediate removal of gaseous and/or vaporized substances generated by the application of laser energy.

It is another object of this invention to provide a laser energy delivery tip element by which a surgeon can apply laser energy and be able to clearly view the site of such energy application by the immediate removal through the same tip element of any gaseous and/or vaporized substances generated during use of the laser surgical tool.

It is yet another object of this invention to provide a laser energy delivery tip element which, by the selection of an appropriately sized single optical fiber, facilitates the delivery of sufficient laser energy to make precise incisions in an easily viewed manner while simultaneously removing any gaseous and/or vaporized substances.

It is a related further object of this invention to provide a laser energy delivery tip element by which a surgeon can apply laser energy at a rate suitable for cutting through tissues while simultaneously removing from the surgical site any gaseous and/or vaporized substances generated during the operation and, furthermore, enabling the surgeon to utilize the same tip element to deliver a separately controlled cauterization current to cauterize and seal off incised blood vessels quickly and efficiently.

These and other related objects are realized by providing, in a preferred embodiment, a tip element for applying laser energy, wherein the tip element includes an optical fiber having an extended distal end for emitting laser energy, and a foraminous element comprising a second material formed and positioned with respect to the distal end of the laser energy delivering optical fiber so as to intercept a first portion of the emitted laser energy to heat a heat-applying first portion of the foraminous element.

In another aspect of this invention, the foraminous element is connected to a separately actuable electrical source to apply a controlled cauterization current to cauterize severed blood vessels while, simultaneously, immediately removing from the cauterization site any gaseous and/or vaporized substances generated by application of the cauterizing electrical current.

In another aspect of this invention, there is provided a method for controllably applying through a single tip sufficient laser energy for cutting through tissues, a controlled electrical current to perform electrocautery and, simultaneously, removing gaseous and/or vaporized substances during such surgical activity.

These and other related objects and aspects of the invention are realized in embodiments more fully described with reference to the accompanying drawings.

DETAILED DESCRIPTION OF THE PREFERRED EMBODIMENTS

Figure 1:
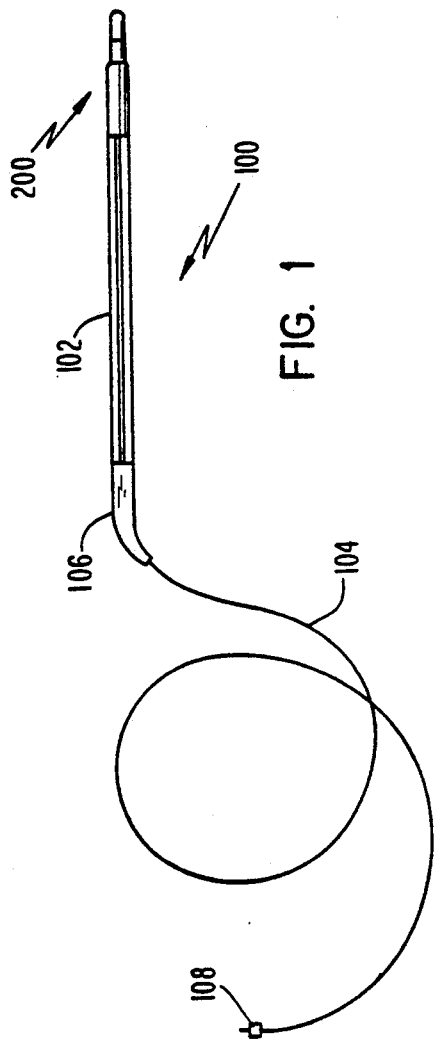
FIG. 1 is a schematic view of a known structure by which laser energy is conveyed from a laser energy source through a hand-held tool to a laser energy delivery tip element.

A surgeon applying laser energy for surgical purposes, e.g., for making incisions through a patient's tissues, typically holds in his or her hand a lightweight, tool 100 into which is fitted an elongate assembly having specifically shaped energized heating element to apply heat by contacting body tissues. As best understood with reference to FIG. 1, such a hand-held surgical tool 100 typically has a slim elongate body 102 connected to a flexible element 104 at a junction 106. The flexible element 104 in known laser systems comprises an outer tubular sheath protectively containing at least a suitable length of an optic fiber connected by a known junction 108 at one end to a source of laser light energy (not shown). In this manner, laser light energy of a suitable wavelength is received at junction 108 from a laser light source located at a convenient distance from the patient, and is conveyed via an optic fiber through flexible element 104, junction 106, and tubular element 102 to a laser energy delivering tip element 200 of the hand-held surgical tool 100.

Laser energy delivery systems, particularly for medical applications when different types of tissues are encountered, are becoming more and more application-specific. Different wavelengths of laser light can be applied to obtain correspondingly different effects on any given tissue. Similarly, when a surgeon encounters a need to use laser light energy of a different wavelength, e.g., in order to cut through a different type of tissue such as muscle or bone, at least with known systems the surgeon is faced with the need to use a laser surgical tool specifically designed to deliver laser energy at the selected wavelength.

For practical reasons, a single optical fiber is often employed to deliver the laser light energy from a laser energy source to and through the surgical tool. Typically, such a single optical fiber must transmit a substantial amount of the received laser energy, i.e., over 85%. There are certain inherent limitations when laser light energy is thus delivered through a single fiber. Thus, if a certain power density of delivered laser energy is required to obtain a specific effect on tissue, then only the end surface of the fiber can be used to emit the energy.

The present invention, as described more fully hereinbelow, provides a practical means of delivering laser light energy and, simultaneously, removing any smoke or other gaseous and/or vaporized substances generated in use of the laser surgical tool regardless of the wavelength of the laser light energy being employed or the tissue treated thereby. It is ideally suited to use with single optical fibers delivering significant amounts of laser energy.

Figure 2:
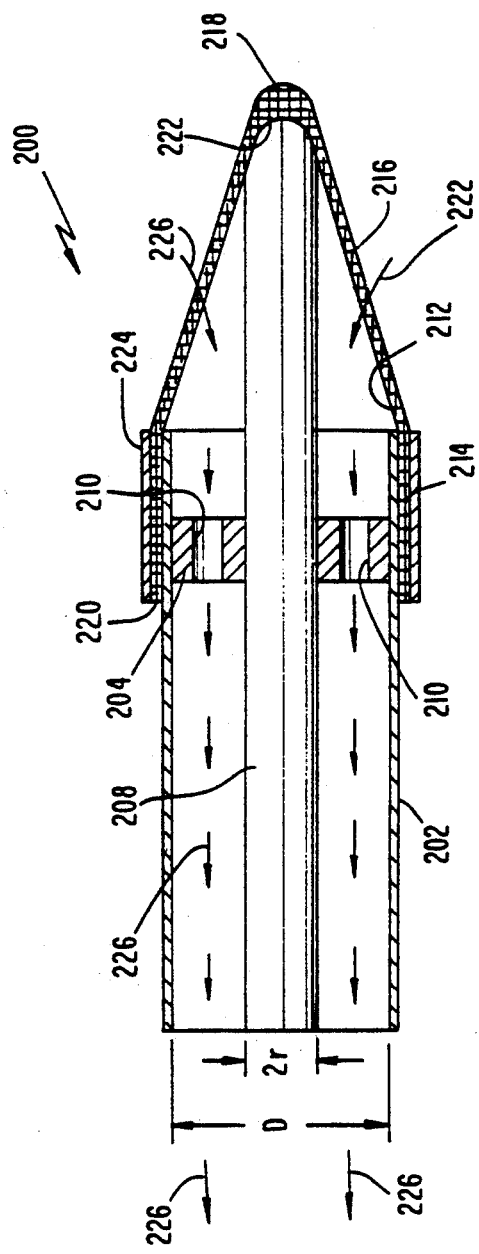
FIG. 2 is a longitudinal cross-sectional view of a laser energy delivery tip element according to a preferred embodiment of this invention.

As best understood with reference to FIG. 2, in a preferred embodiment of this invention, the tip element 200 includes a small length of stainless steel tube 202 having an inside diameter "D". Although stainless steel is believed to be a highly suitable material for this purpose, other metals or alloys may be used instead. Inside tube 202, close to a forward distal end thereof, there is provided a disk-like locator element 204 formed to have a central hole 206 sized to closely receive therethrough an optical fiber 208 which has a diameter "2r".

Figure 3:
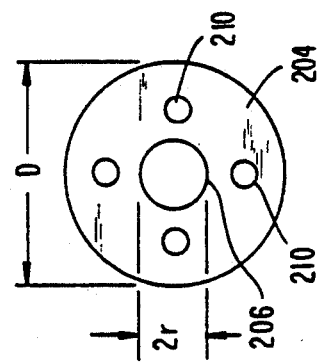
FIG. 3 is a plan view of a spacer element included in the preferred embodiment per FIG. 2 to support and locate a single optical fiber to convey laser energy and, simultaneously, to facilitate the application of suction to withdraw from the surgical site any gaseous and/or vaporized substances generated by application of laser energy.

As best seen in plan view in FIG. 3, locator element 204 is also provided with a plurality of through apertures 210. The number and diameters of apertures 210 are selected to ensure a sufficient flow area through which gaseous and/or vaporized substances are sucked away at a satisfactory rate in the annular space defined between the inside cylindrical surface of tube 202 and the outer surface of optical fiber 208 by the application of suction at a rear end of tube 202. Locator element 204 may be formed of glass, a ceramics material, or even a metal in this particular embodiment. What is important is that locator element 204 be axially long enough to be securely located to support optical fiber 208, withstand forces applied during assembly of the tip element (as more fully described hereinafter), and be able to withstand the working conditions encountered during use of the surgical tool.

Although the diameter of optical fiber 208, and hence of hole 206 receiving it through locator element 204, will depend on the selected laser light wavelength and the application at hand, and an optical fiber diameter within the range 200-1500 $\mu$m should prove satisfactory for most surgical applications.

Fitted to the forward end of tube 202, as best seen in FIG. 2, is a foraminous element 212, which may conveniently be made of a small piece of fine stainless steel wire screen in any known manner. Such a screen preferably has a mesh size such that individual openings therethrough, on an average, have dimensions approximately 1/10th of the diameter of the optical fiber employed in the tip element. Thus, for example, if a 600 $\mu$m optical fiber is selected, then the individual openings through the corresponding screen should have an average size of approximately 60 $\mu$m. Although stainless steel wire screen is preferred for this purpose, what is important is that the selected material be nonreactive to tissues and that it also be able to withstand high temperature without losing physical integrity.

Figure 4B:
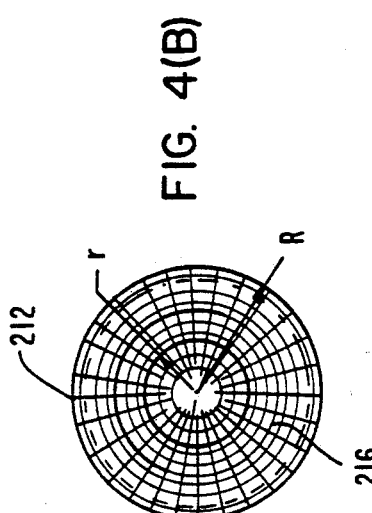
FIG. 4(B) is an end view of the same foraminous element looking toward an energy-delivering convex tip end thereof.
Figure 4A:
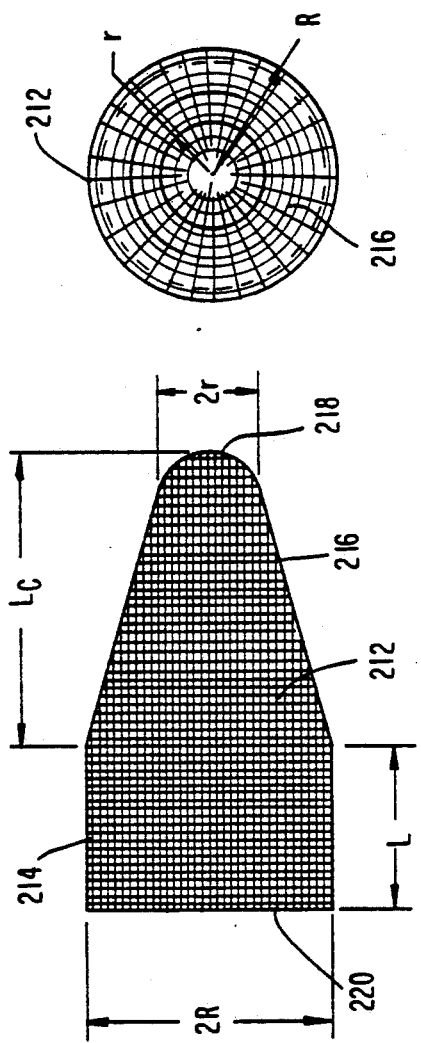
FIG. 4(A) is a side elevation view of a foraminous stainless steel element suitable for inclusion in the preferred embodiment per FIG. 2.

In the preferred embodiment, the foraminous element 212, best seen in FIGS. 4(A) and 4(B), has a generally cylindrical rear portion 214 having a diameter "2R" and a length "L", a right conical portion 216 contiguous therewith at a large end, and a smooth forward end 218 which is free of wrinkles or snags. The rear open end rim 220 of foraminous element 212 preferably also should be free of wrinkles, sharp edges or snags to avoid catching of tissues thereat.

The overall length "$L_c$" of conical portion 216 and the extreme tip portion 218 taken together is a matter of design choice which depends on the diameter of the selected optical fiber 208, the intensity and flux rate of laser light energy desired, and the particular application of interest. It will be understood, however, that if length $L_c$ is made long then there will be a larger surface area to the conical portion 216 and, therefore, a correspondingly larger number of openings through which suction may be applied to the immediate vicinity of the distal end 222 of optical fiber 208. This is best understood with reference to FIG. 2.

In the preferred embodiment per FIG. 2, the forwardmost end of optical fiber 208 is preferably shaped to closely fit inside the forward end of foraminous element 212. Such shaping of optical fiber 208 at its forwardmost end may be obtained by any known technique. What is important to appreciate is that the cylindrical length of optical fiber 208 will serve as a waveguide to convey laser light energy to this shaped end surface 222 and that laser light energy will be emitted almost entirely through surface 222. The purpose in shaping end 222 of optical fiber 208 to fit to the immediately adjacent contacting inside surface of foraminous element 212 is to ensure that the emitted laser light energy will be received by the forwardmost end portion 218 of foraminous element 212 to significantly heat the same under the control of the surgeon.

To ensure that foraminous element 212 remains securely attached to the outside of the forwardmost end of tube 202, i.e., to ensure that it does not fall off during use, a crimping sleeve 224 is slipped over cylindrical portion 214 of the foraminous element and is then crimped by any known means to press thereon. Upon such crimping, crimping sleeve 224 will exert a compressive radially inward force on cylindrical portion 214 of foraminous element 212 and, therethrough, on the outside of tube 202 and thus on the circular peripheral surface of locator element 204. At the same time, the laser light delivering end surface 222 of optical fiber 208 is securely positioned by locator 204 and the cuplike inside shape of forwardmost end 218 of foraminous element 212.

Suction may be applied to the rear end of tube 202 by connection thereat of a suction line (not shown for simplicity) and any known means for applying controlled suction. Such lines and suction mechanisms are well known and will, therefore, not be described in detail. Such a suction line is most conveniently enclosed within flexible element 104.

As will be appreciated, the provision of laser light energy of select wavelength by the surgeon will result in interception of the emitted laser light energy by the forwardmost end 218 of foraminous element 212 and consequent heating thereof. At the very start of the use of such a tip element, it may be expected that some of the emitted laser light energy will simply radiate outwardly through the openings in that portion of foraminous element 212 which is immediately adjacent the shaped laser light delivery end 222 of optical fiber 208. Thus, at least at the very start, there should be available two mechanisms for applying heat energy at the forwardmost end of tip element 200 to tissues under the observation and guidance of the surgeon. It is to be expected, however, that not every bit of the tissue to which energy is applied will be rendered totally into gaseous and/or vaporized substances, i.e., some of the tissue may become carbonized and the resultant carbon particles may clog the openings in portion 218 of the foraminous element. An appreciation of this may be obtained by quick reference to FIG. 5 wherein the bracketed zone designated as "C" generally indicates such a carbonized tip zone of foraminous element 212 immediately surrounding and in contact with laser light delivery end surface 222 of optical fiber 208. Once this happens, laser light energy emitted through surface 222 will be absorbed by the forwardmost end portion of foraminous element 212 and by any carbonized material adhering thereto, so that the carbonized forwardmost tip portion of the tip element will continue to be the hottest available zone which may be applied by the surgeon to effect incision through additional tissue.

Figure 5:
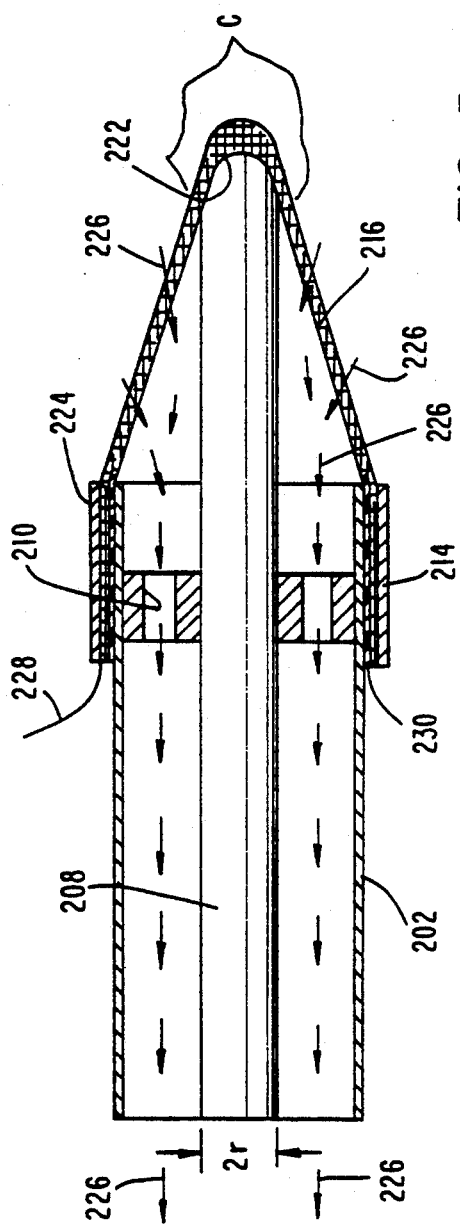
FIG. 5 is a longitudinal cross-sectional view of another preferred embodiment of this invention, including the facility for providing a cauterizing electrical current, to explain the manner in which gaseous and/or vaporized substances may be sucked away from the surgical site during use of the tip element.

As will be appreciated by reference to FIGS. 2 and 5, the application of suction as described earlier will result in a flow, indicated by sequential arrows 226, of ambient air and gaseous and/or vaporized substances generated during use of the tip element, such a flow will pass through the openings of conical portion 216, throughflow apertures 210 of locator element 204, through the annular space between optical fiber 208 and the inside surface of tube 202, and thus immediately away from the operation site.

As noted earlier, the making of incisions through tissues, particular soft body tissues, inevitably involves cutting of blood vessels. Seepage of blood from incised vessels may be stopped by either the surgeon or an assistant promptly cauterizing the cut ends of the vessel. This is a very common practice but, when the operation is performed in a very confined zone, e.g., in a patient's sinuses, it is highly desirable to enable the surgeon to effect cauterization selectively without changing the surgical tool and independently of any assistants. Recent developments in the field of electrocautery involves the application of a controlled electrical current to a cut vessel to generate localized heating of a sufficient magnitude to promptly cauterize the vessel. The cauterizing current enters the patient's tissue at the cauterization site at a relatively high current density over a small area, and then passes through and out of the patient's body over a much larger surface area where the patient is contacted by a conductive surface connected to a terminal of an external electrical source providing the requisite cauterization current.

Figure 8:
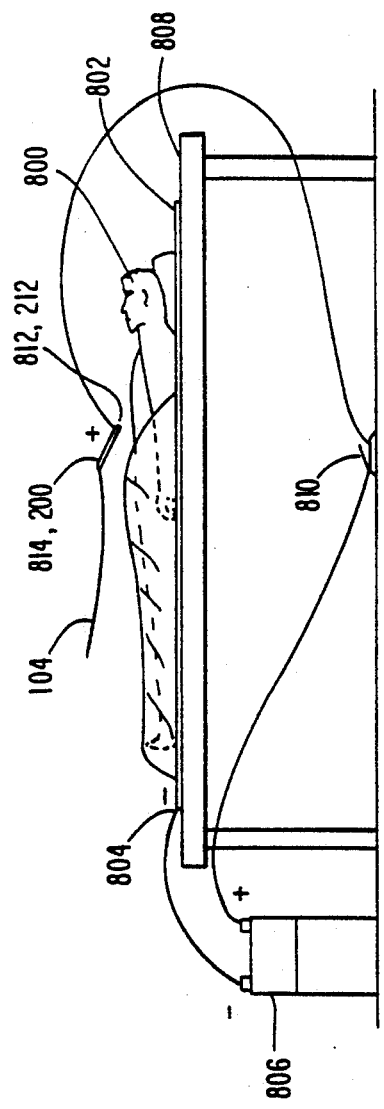
FIG. 8 is a schematic illustration of a circuit arrangement by which a foot-controlled cauterization current may be provided to the tip element.

Reference may be had at this point to FIG. 8 which illustrates schematically a patient 800 lying in electrically conductive contact on a surface of a large conductive pad 802 electrically connected at a point 804 to, for example, the negative terminal of an electrical voltage source 806. Electrically conductive pad 202 is supported on an upper surface of an operating table 808 which may, preferably, be insulated from electrical voltage source 806 or be commonly grounded therewith. Through a user-operated and preferably foot-actuated switch 810, a terminal of electrical voltage source 806 may be connected to a cauterization portion 812 of a hand-held tool 814 by which the surgeon may apply the requisite cauterization current to a cut blood vessel of the patient 800.

In the present invention, as explained more fully hereinbelow, the foraminous element 212 of the laser energy delivery tip element 200 per FIG. 2 corresponds to the cauterization current delivering element 812 in FIG. 8. In this context, what is illustrated as a hand-held cauterization tool 814 in FIG. 8 would correspond to laser surgical tool 100 of FIG. 1, and laser light energy would be delivered thereto by an optical fiber contained within sheath 104.

Referring now to FIG. 5, a modified form of the preferred embodiment illustrated in FIG. 2 has an electrical terminal 228 preferably crimped between crimping element 224 and the outside surface of cylindrical portion 214 of foraminous element 212. Any alternative attachment means may be employed, e.g., an end of electrical terminal 228 may be brazed or silver-soldered to the open end of an electrically conductive foraminous element 212. Naturally, to avoid the passage of electrical current from foraminous element 212 to tube 202, it is necessary to provide an electrically insulating layer 230 between the outside surface of tube 202 and the inside surface of cylindrical portion 214 of foraminous element 212. Such an insulating layer 230 may take the form of a suitable length of Teflon ™ tubing, or a suitably sized strip of any inert electrically insulating material such as Teflon ™, Mylar ™ or mica. Sufficient electrical insulation may also be provided simply by coating the outer forward end surface of tube 202 with a plastics or resinous material prior to fitting thereon of foraminous element 212.

By the structure described in the immediately preceding paragraphs, the surgeon is provided various facilities for selectively incising or cauterizing tissues while, simultaneously, removing any odors, smoke, gaseous and/or vaporized substances generated during either activity from the operation site. Specifically, in any known manner, e.g., by a handactuated switch on the surgical tool, the surgeon may apply a controlled flow of laser light energy to heat the forwardmost end 218 of tip element 200 to effect incisions. The application of suction to the rear end of tube 202, as previously described, may be effected by a small-gauge suction line contained lengthwise within flexible sheath-like element 104 and connected to a suction source. Furthermore, by the structure illustrated in FIGS. 5 and 8, by selective operation of a foot switch 810 the surgeon can cause a voltage difference to be applied between foraminous element 212 and the body of patient 800. Then, while the surgeon operates footswitch 810 selectively, contact by conical portion 216 and/or the forward end 218 of foraminous element 212 to a cut vessel of the patient would generate the required high current density to cause selective local heating and cauterization of the cut vessel. This occurs without discomfort or harm to the patient since the current thus generated will leave the patient over a relatively large area of his or her body at a relatively low current density. In this manner, the surgeon can operate in a confined space in the patient's body, using a single tool and, by combined actuation of a hand operated switch controlling the flow of laser energy and the foot-operated switch 810 to control a cauterization current, to proceed rapidly and efficiently.

Figure 7:
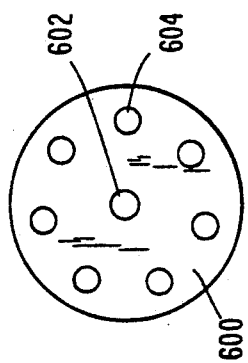
FIG. 7 is a plan view of the rear end of the multi-lumened fiber locating element per the embodiment of FIG. 6.
Figure 6:
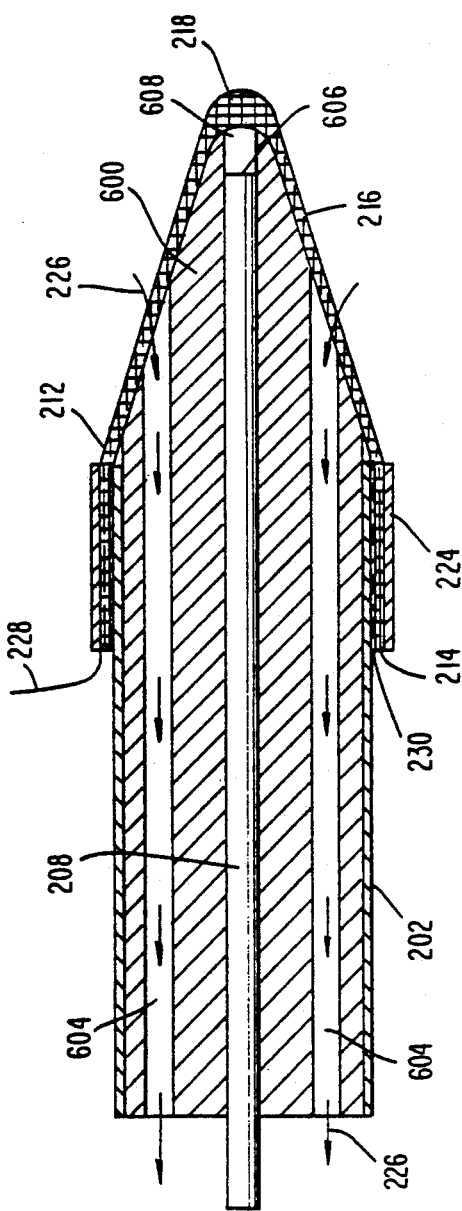
FIG. 6 is a longitudinal cross-sectional view of yet another embodiment of this invention, including an elongate, shaped, optical fiber supporting inner element formed with a plurality of lumens to facilitate delivery of laser energy for cutting, a separately controlled electrical cauterization current through the same tip element, and removal of gaseous and/or vaporized substances from the site where energy is applied.

FIGS. 6 and 7 illustrate another embodiment of the present invention. Referring to FIG. 6, it will be seen that the overall structure has many aspects and features in common with the preferred embodiment according to FIG. 5. The structure illustrated in FIG. 6 thus has tube 202 with an insulating sleeve or layer 230 around a forward end thereof, a foraminous element 212 having a cylindrical portion 214 crimped onto insulating layer 230 by a crimping sleeve 224, and an optical fiber 208 to convey laser light energy of a selected wavelength from a laser light source (not shown). A suction line (not shown) is also provided as described earlier in relation to the embodiment of FIG. 5. As before, foraminous element 212 also has a conical portion 216 and a forward closed end 218.

In the embodiment of FIGS. 6 and 7, in place of the disk-like laser fiber locator element 204, there is provided a relatively longer multi-lumened laser fiber locator element 600 formed to have a central laser fiber receiving lumen 602 and a plurality of throughflow lumens 604. Multi-lumened locator element 600 has a cylindrical portion having an outside diameter sized to closely fit into tubular element 202 and a forward tapered portion shaped and sized to fit closely into conical portion 216 of foraminous element 212. Multi-lumened locator element 600 may be made of the same materials as the earlier-described disk-like locator element 204.

As with the embodiment per FIG. 5, an electrical terminal 228 may be crimped between crimping element 224 and the outside surface of cylindrical portion 214 of foraminous element 212 to enable the provision of a user-controlled electrical voltage and current to effect cauterization as previously described.

Any gaseous and/or vaporized substances generated by the application of laser energy and/or a cauterization current may be removed from the operational site by the application of suction, as previously described, to the rear end of tube 202 and multi-lumened locator element 600 contained therein. Sequential arrows 226, as before, indicate the manner in which such gaseous and/or vaporized substances flow through lumens 604 in essentially the same manner as such flows passed through apertures 210 in locator element 204 in the earlier-described embodiments.

There is one very important respect in which the embodiment per FIGS. 6 and 7 differs from the previously-described embodiments. As best seen in FIG. 6, optical fiber 208 ends at a transverse laser energy emitting face 606. This face 606 of optic fiber 208 is preferably disposed normal to the longitudinal direction of fiber 208 within multi-lumened locator element 600. As indicated in FIG. 6, end face 606 of optical fiber 208 is recessed from an inside surface of end portion 218 of foraminous element 212 so as to leave a small space 608. Such a structure ensures that no portion of optical fiber 208 makes contact with either foraminous element 218 or any carbonized material that may be located in the openings thereof.

Experience shows that the laser light delivering end faces of optical fibers maintain their physical integrity and useful life longer if direct contact with tissues can be avoided during use. The embodiment illustrated in FIGS. 6 and 7 thus permits a surgeon to enjoy all the advantages of the earlier described embodiments and, for many practical uses, also provides prolonged useful life for the tip element. It will be appreciated that in the embodiment per FIGS. 6 and 7, laser light emitted from end face 606 of optic fiber 208 will experience very little divergence, hence the delivered laser light energy will be delivered to a relatively small area of the forwardmost portion 218 of foraminous element 212. Such a high intensity delivery of laser light energy and the corresponding high temperatures thus obtained may be utilized beneficially in certain surgical applications, e.g., to cut through dense tissues like bone or tendons.

Figure 9A:
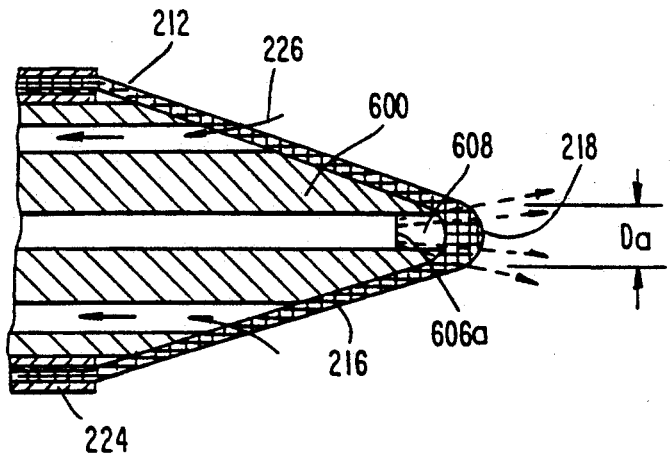
FIGS. 9A-9C illustrate optional structural arrangements at the laser light delivery end of an embodiment according to FIG. 6.

FIG. 9A is an illustration of the laser light delivery tip end portion of the embodiment per FIG. 6, wherein the slightly divergent laser light beam emitted from a flat normal end surface 606a of optic fiber 208 is graphically depicted by a plurality of broken lines with forwardly directed arrowheads. As will be readily appreciated, if multi-lumened laser fiber locator element 600 is formed of a clear, light-transmitting material such as silica, quartz or the like, the slightly divergent beam of laser light energy will pass through the distal end thereof and be received by an inner surface of the forwardmost portion 218 of foraminous element 212. For purposes of discussion and comparison with other optional arrangements, there is indicated a corresponding area of diameter "$D_a$" of the laser light receiving surface of the forwardmost portion 218 of the foraminous element for this arrangement.

Figure 9B:
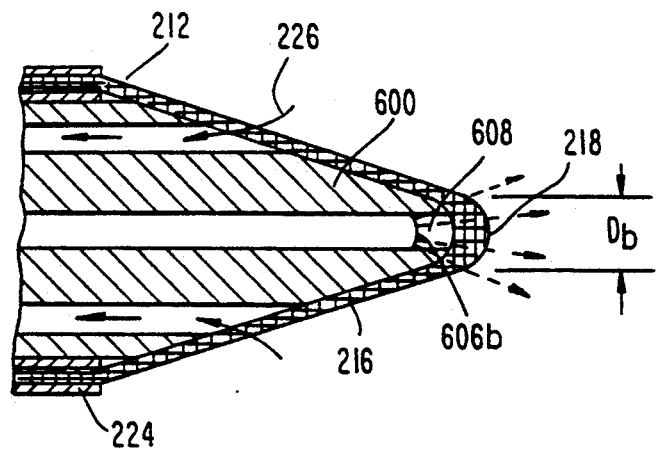

For certain applications, it may be desirable to have an even larger area of the forwardmost portion 218 of the foraminous element 212 heated in an arrangement with a light-transmitting multi-lumened laser fiber locator element 600. As illustrated in FIG. 9B, a very simple solution would be to form the distal end of optic fiber 208 so that it has a curved convex end surface 606b. As will be readily appreciated, the curved extreme end portion of such an optic fiber 208 will serve as a convex lens and enhance the divergence of the emitted laser light energy. Thus, even if the curved end surface 606b is not recessed as far as the plane surface 606a, due to the higher divergence of the emitted laser light beam a larger area, corresponding to a larger diameter "$D_b$" of the forwardmost portion 218 of the foraminous element 212 will be heated by the delivered laser light energy.

Figure 9C:
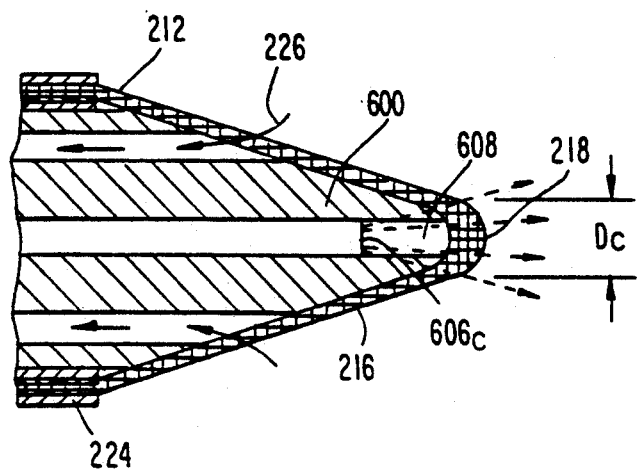

If it is decided, from considerations of cost or otherwise, that it is preferable to utilize an optic fiber 208 with a normal flat laser light energy delivery end, but greater divergence of the laser light beam is desired, another option would be to recess end surface 606c further into the central lumen of multi-lumened optic fiber locator element 600. This is illustrated in FIG. 9C. Due to the greater distance between the distal end surface 606c of optic fiber 208 and the inside surface of the forwardmost portion 218 of the foraminous element, a relatively large area of the foraminous element will receive the emitted laser energy and be heated thereby. In other words, simply by recessing the flat normal distal laser light delivery end surface of optic fiber 208 and using a light-transmitting multi-lumened optic fiber locator element 600, it is possible to heat a larger area corresponding to a diameter "$D_c$" than was possible with the arrangement of FIG. 9A which heated an area of a relatively smaller diameter "$D_a$".

Persons of ordinary skill in the art will immediately appreciate that by further modification of the arrangement illustrated in FIG. 9B, i.e., wherein the convex laser light delivering end surface 606b of optic fiber 208 is recessed even further into the central lumen of multi-lumened optic fiber locator element 600, one can heat an even larger surface area of the forwardmost portion 218 of the foraminous element. Such variations and modifications may readily be tried by a potential user to arrive at the optimum solution for a given application. Correspondingly, a manufacturer of such devices can offer a variety of predetermined sizes, geometries and materials for various elements of the combination described in detail in the preceding paragraphs.

Persons skilled in the art of manufacturing laser equipment generally, and laser surgical equipment in particular, will immediately appreciate that elements such as locator element 204 or multi-lumened locator element 600, stainless steel screen shaped to form foraminous element 212, crimping element 224, or insulating sleeve 230 can all be readily manufactured in quantity at relatively low expense. The finally assembled surgical tip element, in any of the embodiments described herein, can thus be provided and advantageously utilized at a relatively low cost. Such tip elements can, therefore, be inexpensive disposable elements of a combined cutting and cauterizing surgical tool in which gaseous and/or vaporized substances generated during use are immediately removed so that the surgeon may clearly see what he or she is doing at all times and with a single hand-held tool and a foot-actuated switch perform complex and precise surgery efficiently.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A tip element for applying laser energy, comprising:
   an optical fiber comprising a laser light transmitting first material having an extended distal end for emitting laser energy; and
   a foraminous element comprising a second material, formed and positioned with respect to said distal end so as to intercept a first portion of said emitted laser energy, whereby a heat-applying first portion of said foraminous element is heated by laser energy transmitted thereto solely through said optical fiber.

2. The tip element according to claim 1, wherein:
   a second portion of said foraminous element is disposed to permit throughflow of any gaseous or vaporized products generated by application of said heat-applying first portion to an object during use of the tip element.

3. The tip element according to claim 2, wherein:
   said first portion of said foraminous element is formed to have a convex distal end and said second portion of said foraminous element is generally conical in shape, said second portion being contiguous at a small end with said convex distal end and at a large end contiguous with a generally cylindrical third portion of said foraminous element.

4. A tip element for applying laser energy, comprising:
   an optical fiber comprising a laser light transmitting first material, having an extended distal end for emitting laser energy;
   a foraminous element comprising a second material, formed and positioned with respect to said distal end so as to intercept a first portion of said emitted laser energy, whereby a heat-applying first portion of said foraminous element is heated;
   a tubular element comprising a third material and having a distal end disposed to surround said distal end of said optical fiber, said distal end of the tubular element being shaped ad sixed to closely fit into said third portion of said foraminous element; and a perforated locating element supported inside said tubular element, having a first opening sized to closely receive said single optical fiber therethrough to support the same and having at least one flow opening to permit said throughflow to pass therethrough, wherein a second portion of said foraminous element is disposed to permit throughflow of any gaseous or vaporized products generated by application of said heat-applying first portion to an object during use of the tip element, and said first portion of said foraminous element is formed to have a convex distal end and said second portion of said foraminous element is generally conical in shape, said second portion being contiguous at a small end with said convex distal end and at a large end contiguous with a generally cylindrical third portion of said foraminous element. tubular element being shaped and sized to closely fit into said third portion of said foraminous element; and a perforated locating element supported inside said tubular element, having a first opening sized to closely receive said single optical fiber therethrough to support the same and having at least one flow opening to permit said throughflow to pass therethrough.

5. The tip element according to claim 4, further comprising:

connecting means for connecting said third portion of said foraminous element to said distal end of said tubular element.

6. The tip element according to claim 5, wherein:

said connecting means comprises an element shaped and sized to be crimped around an outside of said third portion of said foraminous element with said distal end of said tubular element positioned therein, said crimping element having a smooth outer surface upon being crimped.

7. The tip element according to claim 6, further comprising:

an electrically insulating sleeve element, fitted between said distal end of said tubular element and said third portion of said foraminous element so as to electrically insulate them from each other; and an electrical connection element attached to said third portion of said foraminous element to enable connection thereof to an electrical source.

8. The tip element according to claim 6, wherein:

said locating element is formed as a disk and is located within said tubular element and crimped cylindrical element.

9. The tip element according to claim 8, wherein:

said distal laser energy emitting end of said optical fiber is formed and disposed to fit to an inside surface of said first portion of said foraminous element.

10. The tip element according to claim 6, wherein:

said locating element has a generally cylindrical portion shaped and sized to closely fit inside said tubular element and a generally conical portion shaped and sized to closely fit inside said second portion of said foraminous element, and said at least one flow opening in said locating element is formed as a longitudinally elongate lumen.

11. The tip element according to claim 10, wherein:

said laser energy emitting end of said optical fiber is flat and is normal to a longitudinal direction of said optical fiber thereat, and said flat end of said optical fiber is recessed inside said first opening in said locating element so as to be disposed at a predetermined distance from an adjacent inside surface of said first portion of said foraminous element.

12. The tip element according to claim 7, wherein:

said locating element is formed as a disk and is located within said tubular element and said crimped cylindrical element, further comprising a user-operated means for controlling an electrical voltage applied to said foraminous element.

13. The tip element according to claim 7, wherein:

said locating element has a generally cylindrical portion shaped and sized to closely fit inside said tubular element and a generally conical portion shaped and sized to closely fit inside said second portion of said foraminous element, said at least one flow opening in said locating element is formed as a longitudinally elongate lumen, and further comprising a user-operated means for controlling an electrical voltage applied to said foraminous element.

14. The tip element according to claim 1, wherein:

said foraminous element is formed to have a plurality of through openings which have an average dimension approximately 10% of a diameter of said single optical fiber.

15. The tip element according to claim 14, wherein:

said foraminous element is formed from a wire screen.

16. The tip element according to claim 14, wherein:

said second material comprises stainless steel.

17. The tip element according to claim 4, wherein:

said tubular element comprises stainless steel.

18. The tip element according to claim 4, wherein:

said perforated locating element is formed of a ceramics material.

19. The tip element according to claim 7, wherein:

said electrically insulating sleeve element comprises a material selected from a group consisting of mica, Teflon © and Mylar ©.

20. The tip element according to claim 12, further comprising:

an electrically conductive object-supporting element formed to support an object by contacting the object over a large enough area to provide a predetermined low current density return path to an electrical current generated by said user-controlled electrical voltage applied to said object via said foraminous element during use of said tip element.

21. The tip element according to claim 10, wherein:

said locating element is formed of a light-transmitting material.

22. The tip element according to claim 10, wherein:

said locating element is formed of a light-transmitting material, said laser energy emitting end of said optical fiber is flat and is normal to a longitudinal direction of said optical fiber thereat, and said flat end of said optical fiber is recessed inside said first opening in said locating element so as to be disposed at a predetermined distance from an adjacent inside surface of said first portion of said foraminous element so that a portion of laser light beam emitted from the flat end of the optical fiber diverges and passes through a distal end portion of the locating element.

23. The tip element according to claim 10, wherein:
said locating element is formed of a light-transmitting material,
said laser energy emitting end of said optical fiber has a curved convex shape, and
said convex end of said optical fiber is recessed inside said first opening in said locating element so as to be disposed at a predetermined distance from an adjacent inside surface of said first portion of said foraminous element so that a portion of laser light beam emitted from the convex end of the optical fiber diverges and passes through a distal end portion of the locating element.

* * * * *